United States Patent [19]
Toth et al.

[11] 3,966,726
[45] June 29, 1976

[54] PROCESS FOR THE PRODUCTION OF CYCLIC CARBOXYLIC ACID IMIDES

[75] Inventors: Anton Toth; Gerhard Meyer, both of Obernburg, Germany

[73] Assignee: Akzo N.V., Arnhem, Netherlands

[22] Filed: Sept. 8, 1972

[21] Appl. No.: 287,520

[30] Foreign Application Priority Data
Sept. 23, 1971 Germany............................ 2147535

[52] U.S. Cl. ...................... 260/249.8; 260/250 BN; 260/256.4 N; 260/272; 260/294.8 C; 260/295 M; 260/295.5 B; 260/326 R; 260/306.8 R; 203/53; 203/59; 203/63; 203/96
[51] Int. Cl.².................................... C07D 251/52
[58] Field of Search................ 260/295 M, 295.5 B, 260/326 R, 294.8 C, 256.4 N, 250 BN, 272, 249.8, 306.8; 203/DIG. 6

[56] References Cited
UNITED STATES PATENTS
3,072,725   1/1963   Surman.......................... 203/DIG. 6

Primary Examiner—Alan L. Rotman
Attorney, Agent, or Firm—Johnston, Keil, Thompson & Shurtleff

[57] ABSTRACT

In a process for reacting an aromatic or hydroaromatic alicyclic or heterocyclic dicarboxylic acid or its anhydride with an aliphatic or aromatic alicyclic or heterocyclic mono- or di-amine to produce an N-substituted dicarboxylic acid imide with a splitting off of water, the improvement of carrying out the reaction in a liquid solvent mixture consisting essentially of a non-polar organic solvent and a strongly polar organic solvent which together form a ternary azeotrope with water at reaction temperatures between about 40°C. and 160°C. The imide products are generally known for use as intermediates and final products in a number of industries.

10 Claims, No Drawings

PROCESS FOR THE PRODUCTION OF CYCLIC CARBOXYLIC ACID IMIDES

It is known that N-substituted cyclic carboxylic acid imides can be prepared by reaction of amines with dicarboxylic acid anhydrides. In this synthesis, there is obtained as an intermediate the corresponding N-monosubstituted dicarboxylic acid monoamide which is then converted into the N-disubstituted dicarboxylic acid imide by splitting off water with the aid of phosphorus pentoxide, phosphorus trichloride or acetic anhydride sodium acetate. The cyclic imide can also be obtained directly by melting the anhydride with the amine or by reaction of the two reactants in an inert solvent. (Houben-Weyl, Methoden der Organischen Chemie, Georg Thieme Verlag, Stuttgart, Vol. XI, 2 (1958), pages 16–18, and Chemical Reviews, 1970, Vol. 70, No. 4, pages 439 ff.).

Of the two known single-stage processes, the only useful process for a technical or commercial production of the imide is that in which the reaction takes place in a solvent medium. For this purpose, there have been used either polar solvents or non-polar solvents. By using a non-polar solvent, one must work in a heterogeneous phase and take into account all of the disadvantages associated therewith, because most amines are insoluble or only slightly soluble in non-polar solvents. On the other hand, the use of a polar solvent does not yield a satisfactory result because the miscibility of this solvent with the water split off in the reaction leads to an undesirable shift of equilibrium between the amide and imide products, thereby resulting in substantially smaller yields.

The best results have been achieved in the prior art by use of glacial acetic acid, e.g., as disclosed in Wanag, Ber. 75 (1942), pages 719–725. In the process, nearly quantitative yields are obtained but only if the anhydride is added in an at least 0.5 to 1 molar excess. The extra introduction of the acid anhydride makes this process disadvantageous, especially due to the added process stages or steps required for separation and recovery of the excess unreacted anhydride.

One object of the present invention is to provide a relatively simple, single stage process for the production of N-substituted cyclic dicarboxylic imides from amines and o-dicarboxylic acids or their anhydrides whereby one can achieve good to excellent yields on a commercial basis. Another object of the invention is to provide a process which is widely applicable to different o-dicarboxylic acids or anhydrides as well as to various mono- and di-amines. Other objects and advantages of this invention will become more apparent upon consideration of the following detailed disclosure.

It has now been found, in accordance with the present invention, that a substantial improvement can be achieved in the reaction of an ortho-dicarboxylic acid or its anhydride of the formula

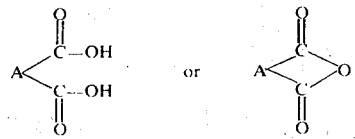

wherein A is a divalent aromatic or hydroaromatic and alicyclic or heterocyclic organic radical, with an aliphatic or an aromatic alicyclic or heterocyclic mono- or di-amine to produce an N-substituted cyclic dicarboxylic acid imide, provided that the reaction is carried out in a liquid solvent mixture consisting essentially of a non-polar organic solvent and a strongly polar organic solvent which form a ternary azeotrope with water. The reaction is generally carried out at a temperature of between about 40°C. and 160°C.

As non-polar solvents, one can generally use benzene, toluene, xylene, ethylbenzene and similar alkyl-substituted aromatic liquid organic solvents. The polar solvent can be broadly selected as an alcohol, e.g., the alkanols such as ethanol, propanol, butanol and the like, or an organic base such as pyridine, picoline, lutidine, quinoline and the like. The so-called dipolar aprotic solvents are especially useful, e.g., readily available solvents such as dimethylformamide, dimethylacetamide, dimethylsulfoxide, acetonitrile, hexamethylphosphoric acid triamide and the like. For ease in recovery, both the polar and non-polar solvent are preferably water-immiscible or only very slightly miscible in water. The following combinations of the non-polar and polar solvents have been found to be especially suitable for use in the solvent mixture according to the invention:

Xylene/dimethylformamide;
Xylene/dimethylacetamide;
Xylene/dimethylsulfoxide;
Toluene/pyridine;
Toluene/picoline;
Benzene/acetonitrile;
Xylene/pyridine;
Xylene/picoline; and
Xylene/lutidine.

One can readily select these and other combinations of a non-polar and polar organic solvent in order to provide a mixture which forms a ternary azeotrope with water, preferably such that the boiling point of the resulting mixture is maintained within the appropriate range of reaction temperatures. The boiling points of individual azeotropic mixtures are either known or can be easily determined by simple preliminary tests.

Although the relative proportions of the polar to non-polar solvent in the solvent mixture can be widely selected, it has been found to be especially preferred to use a solvent mixture consisting of about 10 to 20 percent by volume of the polar solvent to about 90 to 80 percent by volume of the non-polar solvent. If the process is being carried out with a very difficultly soluble amine, it is recommended that the proportion of the polar solvent be extended up to about 30 percent by volume. Accordingly, the proportions by volume of polar:non-polar solvent in the solvent mixture will usually be maintained in a range of about 1:9 to 3:7, preferably about 1:9 to 2:8.

The process of the invention not only leads to very good yields in the reaction of individual o-dicarboxylic acids or their anhydrides with individual amines but is also very broadly applicable to many coreactants with excellent results. The invention thus affords a selection of a large number of acid or anhydride reactants as well as amines to produce a relatively large class of useful imide products of the formula

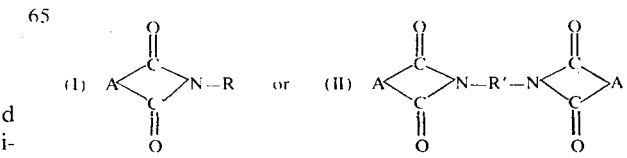

wherein A has the same meaning noted above for the o-dicarboxylic acid or anhydride reactant and R or R' is the organic residue of a mono- or diamine, respectively.

The radicals —A—, —R and —R'— can be unsubstituted or substituted as obtained from the correspondingly unsubstituted or substituted o-dicarboxylic acids and amines as initial reactants. In general, it is particularly appropriate to select substituents such as halogen and especially iodine, bromine and chlorine, lower alkyl and especially methyl or ethyl, lower alkoxy and especially methoxy or ethoxy, or other common substituents such as nitro, hydroxy, mercapto, or esterified or neutralized acid groups such as methyl or ethyl carboxylate and sodium or potassium sulfonate, all of these substituents being preferably located on an aromatic ring.

The utility of both the unsubstituted and substituted products is known as will be apparent from the Chemical Reviews reference, supra, and other references, either directly or as known intermediates for such purposes as providing brightening agents in the textile and laundry industries, color developers in the photographic industry, or various biocides including fungicides, bacteriocides and insecticides. Attention is directed to such references as U.S. Pat. No. 2,911,410 and Chem. Abstracts, Vol. 54, p. 7388 (1960) for developers; British Pat. No. 609,488 and Chem. Abstracts, Vol. 57, p. 13, 695 for substituted phthalimides as antihypotensive agents; and Chem. Reviews, supra, page 648, for phthalimide derivatives which inhibit the growth of the polio virus.

Examples of suitable and especially preferred carboxylic acids which may also be used in the form of their anhydrides are as follows: phthalic acid; tetrahydrophthalic acid; tetrachlorophthalic acid; tetrabromophthalic acid; 3-nitrophthalic acid; quinolinic acid; 4-nitrophthalic acid; 3-acetamido-phthalic acid; 4-acetamido-phthalic acid; 3-bromo-phthalic-acid; 4-bromo-phthalic-acid; 3-chloro-phthalic-acid; 4-chloro-phthalic-acid.

Examples of suitable amines for the process of the invention are as follows: alkylamines such as n-decylamine, n-octadecylamine, tetramethylenediamine, decamethylenediamine, 1,2-diaminopropane, 2-N-diethylamino-aminoethane; 1,3-diamino-propane; 1-amino-5-cyano-propane; 2-amino-4-methyl-mercapto-1-butanol; 2-amino-3-methylpentane; 2-amino-4-methylpentane; 1-amino-butane; 2-amino-2-methyl-1-propanol; aryl and especially phenylamines such as aniline, 2-nitroaniline, 2-chloroaniline, 2-aminophenol, 3-aminophenol, 4-aminophenol, 2-aminothiophenol, 2-aminophenetol, 4-aminophenetol, p-aminobenzenesulfonic acid salts of alkali metals such as sodium or potassium, p-amino-diethylaniline, 2-chloro-4-nitroaniline, 2-nitro-4-chloro-aniline, 4-amino-1,2-dimethylbenzene, 3,4-dichloroaniline, p-xylidine, 3-chloro-4-methyl-aniline, m-xylidine, 2,4-dinitroaniline, 3,5-dichloroaniline, 1,3-diaminotoluene, 3,4-diaminotoluene, 1,6-dichlorophenylenediamine, 4,4'-diaminodiphenylmethane, 1,5-diaminoanthraquinone; 4,4'-diaminodiphenyloxide, 4,4'-diaminodiphenylsulfone; or other aromatic heterocyclic amines such as aminopyrazine, 2-aminopyridine, 2-aminothiazole, 2-amino-4-methylpyridine; 6-amino-3-methyl-pyridine; 2-amino-4-methyl-pyrimidine; ammeline; 2,6-diaminopyridine; 3-amino-pyridine; 4-amino-pyridine.

According to the invention, the following exemplary compounds are capable of being produced smoothly and in good yields in accordance with the procedure used in the working examples below:
 phthalimido-2-nitrobenzene,
 phthalimido-2-chlorobenzene,
 phthalimido-n-hexane,
 N-phthalimido-octadecane,
 2-N-phthalimido-phenol,
 2-N-phthalimido-phenetole,
 4-N-phthalimido-phenetole,
 1-amino-5-N-phthalimido-anthraquinone,
 2,6-dichloro-4-N-phthalimido-aniline,
 1,10-N,N'-diphthalimido-decane,
 4-N-phthalimido-5-chloro-nitrobenzene,
 1-N-phthalimido-2-nitro-4-chlorobenzene, 1,3-N,N'-diphthalimido-propane,
 1,2-N,N'-diphthalimido-propane,
 2-amino-4-N-phthalimido-toluene,
 4-(N-phthalimido)-N-dimethylaniline,
 1-(N-phthalimido)-3,4-dimethylbenzene,
 1-(N-phthalimido)-3,4-dichlorobenzene,
 4,4'-(N,N'-ditetrahydrophthalimido)-diphenylmethane,
 1-(N-tetrahydrophthalimido)-2,5-dimethylbenzene,
 2-(N-tetrahydrophthalimido)-phenol,
 1-(N-tetrahydrophthalimido)-3-chloro-4-methylbenzene,
 1-(N-tetrahydrophthalimido)-2-N'-diethylaminoethane,
 N-tetrahydrophthalimido-octadecane,
 N-tetrahydrophthalimido-hexane,
 1-(N-tetrahydrophthalimido)-3,4-dimethyl-benzene,
 2-(N-phthalimido)-thiophenol,
 N-2,4-dinitroanilinophthalimide,
 N-phthalimido-pyrazine,
 2-(N-tetrahydropthalimido)-thiophenol,
 2-(N-tetrahydrophthalimido)-phenetole,
 4-(N-tetrahydrophthalimido)-phenetole,
 1,4-(N,N'-diphthalimido)-butane,
 4-(N-tetrachlorophthalimido)-phenol,
 3-(N-tetrachlorophthalimido)-phenol,
 2-(N-tetrachlorophthalimido)-phenetole,
 4-(N-tetrachlorophthalimido)-phenetole,
 2-(N-tetrachlorophthalimido)-pyridine,
 N-tetrachlorophthalimido-hexane,
 N-tetrachlorophthalimido-octadecane,
 2-(N-tetrachlorophthalimido)-thiazole,
 2-(N-tetrachlorophthalimido)-thiophenol,
 4-(N-phthalimido)-2,6-dichloroaniline,
 4-(N-tetrahydrophthalimido)-2,6-dichloroaniline,
 4-(N-tetrahydrophthalimido)-benzoic acid ethyl ester,
 1-(N-tetrachlorophthalimido)-3,4-dichlorobenzene,
 4-(N-tetrachlorophthalimido)-N,N-diethylaniline,
 2-(N-tetrabromophthalimido)-phenetole,
 2-(N-quinolinimido-phenol,
 2-(N-quinolinimido)-thiophenol,
 4-(N-quinolinimido)-3-amino-toluene,
 2-(N-quinolinimido)-pyridine,
 N-(4-phenyl sulfonic acid potassium salt)-tetrahydrophthalimide,
 N-(4-phenyl sulfonic acid potassium salt)-phthalimide, 2-(N-quinolinimido)-thiazole, 2-N-(3-nitrophthalimido)-phenetole,
2-N-(3-nitrophthalimido)-pyridine,
2-N-(3-nitrophthalimido)-phenol.

The process of the invention is preferably carried out such that the amine is dissolved in the polar solvent and the dicarboxylic acid or its anhydride is dissolved in the non-polar solvent, both solvents are then brought together and heated to begin the reaction. Over the course of the reaction, the temperature is raised up to the boiling point of the reaction mixture, and the water produced by the reaction is aceotropically distilled off with a portion of the solvent medium. The resulting distillate is cooled, the aqueous phase separated therefrom and the organic phase returned to the reaction mixture. It has also been found to be especially favorable to preheat the solution of the dicarboxylic acid or its anhydride to about 40° to 90°C. before admixing it with the amine solution. This preheating procedure provides higher yields.

In general, the process according to the invention is conducted at temperatures within the range of about 40° to 160°C. The adjustment of the reaction temperature depends partly upon the individual reactants.

Dicarboxylic acids and their anhydrides which do not contain any other reactive groups can be readily reacted at the high temperatures of the cited range, for example at temperatures above 140°C. In these instances, the solutions of the amine and the dicarboxylic acid or anhydride can be heated directly to the boiling point after being joined together for the reaction.

Those amines and dicarboxylic acids or anhydrides which contain other reactive substituents or groups tend to react with themselves at such higher temperatures or with each other to form undesirable by-products. For example, if a nitro-substituted dicarboxylic acid or anhydride is reacted with an amine containing a mercapto or thio group, tarry by-products tend to form through reduction of the nitro groups. Further examples of possible side reactions include the splitting off of bromine when using tetrabromophthalic anhydride or the ring opening of a sulfur-containing heterocyclic compound. It has been found, however, that the side reactions can be substantially or completely prevented if the reaction is first conducted at temperatures in the range of about 40° to 70°C. and then raised to the boiling point of the mixture only after complete or substantially complete formation of the halfamide.

When using quinolinic acid, i.e., pyridine-2,3-dicarboxylic acid, it is preferable to conduct the reaction at lower temperatures, for example in the range of about 40°C. up to about 110°C. In the reaction of quinolinic acid with an amine, there first form equal parts by weight of the α- and β-halfamide isomers. Although the α-isomer is very thermally stable, the β-isomer undergoes decarboxylation at higher reaction temperatures so as to reduce the otherwise available yield.

It is necessary, of course, to choose the solvent mixture so as to achieve a ternary azeotropic distillation between the solvents and the water produced in the reaction within the desired temperature range. One usually selects the highest possible temperature for the azeotropic distillation at which side reactions are avoided or at least kept to a minimum as indicated above. The following table provides a few examples of solvent mixtures and the boiling point range of the azeotropic mixture.

| SOLVENT MIXTURE (Percentage by volume) | AZEOTROPE B.P. Range |
| --- | --- |
| 80% xylene + 20% dimethylformamide | 135 – 140°C. |
| 80% toluene + 20% dimethylformamide | 100 – 110°C. |
| 87% xylene + 13% dimethylformamide | 131 – 136°C. |
| 87% xylene + 13% pyridine | 125 – 129°C. |

The solvents are employed in amounts sufficient to fully dissolve the amine reactant as well as the dicarboxylic acid or its anhydride. Both reactants are preferably brought together in stoichiometric equivalent amounts even though a slight excess of either the amine or the dicarboxylic acid or anhydride may be present if desired. There is no special advantage in employing a large excess of either reactant.

The reaction mixture can be worked up in a relatively conventional manner after the reaction has been completed. Thus, after all the water has been separated by azeotropic distillation, the remaining reaction mixture is cooled. This cooling generally causes crystallization of the desired N-substituted carboxylic acid imide in high yields and in almost analytically pure form. In the case of highly soluble reaction products, one can concentrate the reaction mixture in a vacuum distillation and then crystallize the residue from a suitable solvent. The residue or deposit from the reaction can also be completely evaporated to dryness and the crude product purified by sublimation.

With the process of the invention, the N-substituted dicarboxylic acid imides are obtained in high yields and purity. However, it is a special advantage of the invention that the reaction components can be brought together in stoichiometric equivalent amounts so as to greatly facilitate a working up of the reaction mixture and to avoid losses of valuable materials.

In the tabulated set of examples below, provided for the purpose of illustrating the invention, the following solvent mixtures were employed as the initial reaction medium:

| Mixture No. | Non-polar Solvent | Polar Solvent |
| --- | --- | --- |
| I | 70 ml. xylene | 30 ml. dimethylformamide |
| II | 80 ml. xylene | 20 ml. dimethylacetamide |
| III | 90 ml. xylene | 10 ml. dimethylsulfoxide |
| IV | 70 ml. toluene | 30 ml. pyridine |
| V | 80 ml. toluene | 20 ml. picoline |
| VI | 90 ml. toluene | 10 ml. pyridine |
| VII | 80 ml. benzene | 20 ml. acetonitrile |
| VIII | 85 ml. benzene | 15 ml. acetonitrile |
| IX | 90 ml. benzene | 10 ml. acetonitrile |
| X | 80 ml. xylene | 20 ml. pyridine |
| XI | 85 ml. xylene | 15 ml. picoline |
| XII | 90 ml. xylene | 10 ml. lutidine |

The experimental procedure in each instance was as follows:

0.25 mol of the dicarboxylic acid or anhydride was dissolved in the non-polar solvent and 0.25 mol of the amine was dissolved in the polar solvent prior to mixing into a single reaction medium. The solution of the dicarboxylic acid or anhydride was preheated to 90°C. and then mixed in portions with the solution of the amine. Then, the reaction mixture was gradually heated up to its boiling temperature over a period of about 10 to 30 minutes. The azeotrope being distilled off at this boiling temperature was continuously conducted into a water separator. After separation of the aqueous phase, the remaining organic solvent was returned to the reaction mixture. Upon completion of the splitting off and separation of water, the reaction mixture was worked up in the usual manner to crystallize and separate the desired imide product.

In the following table of the examples, there are listed the two reactants, the particular solvent mixture, the imide reaction product and its boiling point and yield.

and preferably 6 to 10 carbon atoms. The amino-substituted pyridine reactant also provides good results.

The process of the invention is subject to some individual variations for reasons given above, but careful selection of the solvent mixture within the prescribed limitations of the present invention leads to surprisingly improved results as well as a much more easily controlled and supervised reaction on a commercial scale.

The invention is hereby claimed as follows:

TABLE

| Ex. No. | O-Dicarboxylic acid or anhydride | Amine | Solvent Mixture | Reaction Product | M.P. °C | Yield % of theory |
|---|---|---|---|---|---|---|
| 1 | Phthalic anhydride | 2-nitroaniline | II | Phthalimido-2-nitrobenzene | 295–6 | 97.0 |
| 2 | Phthalic anhydride | 2-chloroaniline | III | Phthalimido-2-chlorobenzene | 137.8 | 90.6 |
| 3 | Phthalic anhydride | 2-aminophenol | XII | 2-(N-phthalimido)-phenol | 219–222 | 95.5 |
| 5 | Phthalic anhydride | 1,10-diaminodecane | III | 1,10-(N,N'-diphthalimido)-decane | 131 | 87.0 |
| 6 | Tetrahydrophthalic anhydride | 4,4'-diamino-diphenylmethane | VII | 4,4'-(N,N'-di-tetrahydrophthalimido)-diphenylmethane | 202 | 78.8 |
| 7 | Tetrahydrophthalic anhydride | 2-amino-thiophenol | X | 2-(N-tetrahydrophthalimido)-thiophenol | 175 | 67.3 |
| 8 | Tetrahydrophthalic anhydride | 2-amino-phenetole | III | 2-(N-tetrahydrophthalimido)-phenetole | 93–95 | 95.1 |
| 9 | Tetrahydrophthalic anhydride | 4-amino-phenol | IX | 4-(N-tetrahydrophthalimido)-phenol | 112–114 | 94.2 |
| 10 | Tetrabromophthalic anhydride | 2-amino-phenetole | IX | 2-(N-tetrabromophthalimido)-phenetole | 238–241 | 67.4 |
| 11 | Tetrachlorophthalic anhydride | 4-amino-N,N-diethyl-aniline | II | 4-(N-tetrachlorophthalimido)-N,N-diethyl-anilline | 210–212 | 69.8 |
| 12 | Tetrachlorophthalic anhydride | 4-amino-phenol | I | 4-(N-tetrachlorophthalimido)-phenol | 298–301 | 72.2 |
| 13 | Tetrachlorophthalic anhydride | 3-amino-phenol | II | 3-(N-tetrachlorophthalimido)-phenol | 267–268 | 71.5 |
| 14 | Quinolinic acid | 2-amino-phenol | III | 2-(N-quinolinimido)-phenol | 230–232 | 63.4 |
| 15 | Quinolinic acid | 2-amino-thiophenol | II | 2-(N-quinolinimido)-thiophenol | 229–231 | 59.0 |
| 16 | Quinolinic acid | 2-amino-pyridine | VI | 2-(N-quinolinimido)-pyridine | 151–153 | 71.2 |
| 17 | 3-nitrophthalic anhydride | 2-amino-phenetole | V | 2-N-(3-nitrophthalimido)-phenetole | 156 | 92.0 |
| 18 | 3-nitrophthalic anhydride | 2-amino-pyridine | IV | 2-N-(3-nitrophthalimido)-pyridine | 176 | 88.5 |
| 19 | 3-nitrophthalic anhydride | 2-amino-phenol | VIII | 2-N-(3-nitrophthalimido)-phenol | — | 86.6 |

Especially good results are achieved in the process of the present invention when reacting phthalic acid or its anhydride and their mono-substituted derivatives of the formula

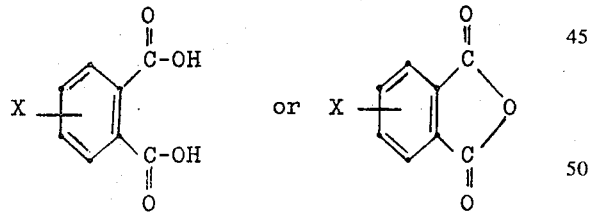

wherein X is hydrogen, bromo, chloro, nitro, methyl, ethyl, methoxy, ethoxy or other relatively inert substituents, with an aromatic monoamine and especially aniline or its mono-substituted derivatives of the formula

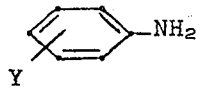

wherein Y is hydrogen, hydroxy, mercapto, methyl, ethyl, methoxy, ethoxy, chloro, bromo, nitro or other relatively inert substituents. Similar good results are achieved with other specific reactants, including for example the alkylamines and alkylene diamines of longer chain length, e.g., from 4 to 18 carbon atoms 1. In a process for the production of an N-substituted cyclic carboxylic acid imide by reacting in a solvent at an elevated temperature between about 40°C. and 160°C.

A. an ortho-dicarboxylic acid or its anhydride of the formula

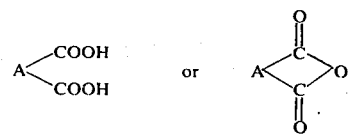

wherein A is a divalent radical, selected from amongst phenylene, or phenylene substituted by halogen, nitro, acetamido, lower alkyl, lower alkoxy; tetrahydrophenylene or pyridylene:
with B. a mono- or di-amine, selected from amongst alkylamine, alkylenediamine, N-alkyl substituted alkylenediamine of up to 18 carbon atoms; phenyl mono- or diamines which may be substituted by halo, nitro, hydroxy, mercapto, lower alkyl, lower alkoxy, mercaptomethyl, mercaptoethyl, methyl or ethyl carboxylate, sodium or potassium sulfonate, or 4,4'-diaminodiphenylmethane, 4,4'-diaminodiphenyloxide, 4,4'-diamino diphenylsulfone, 1,5-diaminoanthraquinone, aminopyrazine, 2-aminopyridine, 2-aminothiazole, 2-amino-4-methylpyridine, 6-amino-3-methylpyridine, 2- amino-4-methylpyrimidine, ammeline, 2,6-diaminopyridine, 3-aminopyridine or 4-aminopyridine the improvement of carrying out said reaction in a liquid solvent mixture consisting essentially of a non-polar organic solvent and a strongly polar organic solvent which form a ternary azeotrope with water at the reaction temperature.

2. A process as claimed in claim 1 wherein said liquid solvent mixture consists essentially of xylene and a polar solvent selected from the class consisting of dimethylformamide, dimethylacetamide, dimethylsulfoxide, pyridine, picoline and lutidine.

3. A process as claimed in claim 1 wherein said liquid solvent mixture consists essentially of toluene and a polar solvent selected from the class consisting of pyridine and picoline.

4. A process as claimed in claim 1 wherein said liquid solvent mixture consists essentially of benzene and acetonitrile.

5. A process as claimed in claim 1 wherein the liquid solvent mixture consists essentially of 80 to 90% by volume of the non-polar solvent and 20 to 10% by volume of the polar solvent.

6. A process as claimed in claim 1 wherein the reaction is carried out at temperatures of 90° to 160°C.

7. A process as claimed in claim 1 wherein the amine as one reactant is dissolved in the polar solvent, the dicarboxylic acid or its anhydride as the other reactant is dissolved in the non-polar solvent, the two resulting solutions are then joined and the resulting mixture heated to the reaction temperature, water resulting from the reaction is azeotropically distilled with a portion of the solvent, the distillate is then cooled and the aqueous phase is separated therefrom while recycling the organic phase to the reaction mixture.

8. A process as claimed in claim 7 wherein the reaction mixture is heated to its boiling point during the course of the reaction in order to continuously azeotropically distill off the water with a portion of the solvent.

9. A process as claimed in claim 7 wherein the non-polar solvent containing the dicarboxylic acid or anhydride reactant is preheated to a temperature of about 40° to 90°C. before being joined with the amine-containing polar solvent.

10. A process as claimed in claim 9 wherein the reaction is carried out at a temperature of from about 90° to 160°C. after joining the two reactants with their solvents.

* * * * *